US008566367B2

(12) United States Patent
Matsue et al.

(10) Patent No.: US 8,566,367 B2
(45) Date of Patent: Oct. 22, 2013

(54) MEDICAL IMAGE INFORMATION SYSTEM, IMAGE SERVER AND CLIENT

(75) Inventors: Kenji Matsue, Nasushiobara (JP); Kenichi Niwa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 878 days.

(21) Appl. No.: 11/866,108

(22) Filed: Oct. 2, 2007

(65) Prior Publication Data
US 2008/0086335 A1 Apr. 10, 2008

(30) Foreign Application Priority Data
Oct. 6, 2006 (JP) .................................. 2006-275255

(51) Int. Cl.
*G06F 17/30* (2006.01)
(52) U.S. Cl.
USPC ......................................................... 707/812
(58) Field of Classification Search
USPC ......................................................... 707/812
See application file for complete search history.

(56) References Cited

U.S. PATENT DOCUMENTS

| 5,948,040 | A * | 9/1999 | DeLorme et al. ............. 701/201 |
|---|---|---|---|
| 6,263,350 | B1 * | 7/2001 | Wollrath et al. ..................... 1/1 |
| 6,615,266 | B1 * | 9/2003 | Hoffman et al. ............. 709/227 |
| 7,130,885 | B2 * | 10/2006 | Chandra et al. .............. 709/206 |
| 7,325,095 | B2 * | 1/2008 | Williams ...................... 711/112 |
| 7,487,308 | B1 * | 2/2009 | Dalal et al. ................... 711/162 |
| 7,746,491 | B2 * | 6/2010 | Ikeda et al. .................. 358/1.15 |
| 2002/0059193 | A1 * | 5/2002 | Decime ............................ 707/3 |
| 2002/0111960 | A1 * | 8/2002 | Irons et al. .................... 707/204 |
| 2002/0138582 | A1 * | 9/2002 | Chandra et al. .............. 709/206 |
| 2003/0195986 | A1 * | 10/2003 | Densmore ..................... 709/245 |
| 2005/0141444 | A1 * | 6/2005 | Hirai ............................. 370/313 |
| 2005/0226405 | A1 * | 10/2005 | Fukatsu et al. ................... 380/1 |
| 2006/0009692 | A1 * | 1/2006 | Fukuda et al. ................. 600/407 |
| 2006/0010013 | A1 * | 1/2006 | Yamatake ......................... 705/2 |

(Continued)

FOREIGN PATENT DOCUMENTS

| JP | 2001-84388 | 3/2001 |
|---|---|---|
| JP | 2001-133874 A | 5/2001 |

(Continued)

OTHER PUBLICATIONS

ASP.NET Custom Error Pages, http://aspnetresources.com/articles/CustomErrorPages, posted on Feb. 1, 2004, pp. 1-17.*

(Continued)

*Primary Examiner* — Sheree Brown
(74) *Attorney, Agent, or Firm* — Oblon, Spivak, McClelland, Maier & Neustadt, L.L.P.

(57) ABSTRACT

Provided is a medical image information system that prepares a diagnosis report for which link information for referring to a medical image stored in an image server is set, and displays a medical image not stored in the image server. The medical image information system includes a reservation request unit that makes a storage location reservation request for the medical image not stored in the image server prior to storing the medical image not stored in the image server, a reservation unit that receives the storage location reservation request and makes reservation for storage location of the medical image not stored in the image server, and a link information setting unit that sets the link information for the reserved storage location.

7 Claims, 5 Drawing Sheets

(56) References Cited

U.S. PATENT DOCUMENTS

| | | | | |
|---|---|---|---|---|
| 2006/0106284 | A1* | 5/2006 | Shouji et al. | 600/118 |
| 2006/0242382 | A1* | 10/2006 | Griess et al. | 711/170 |
| 2006/0271403 | A1* | 11/2006 | Iwasa et al. | 705/2 |
| 2006/0279764 | A1* | 12/2006 | Shimada | 358/1.14 |
| 2007/0064987 | A1* | 3/2007 | Esham et al. | 382/128 |
| 2010/0034442 | A1 | 2/2010 | Minakuchi et al. | |

FOREIGN PATENT DOCUMENTS

| | | |
|---|---|---|
| JP | 2002-73615 | 3/2002 |
| JP | 2002-111987 | 4/2002 |
| JP | 2002-209128 | 7/2002 |
| JP | 2002-269230 | 9/2002 |
| JP | 2002-282213 | 10/2002 |
| JP | 2002-336203 | 11/2002 |
| JP | 2004-70619 | 3/2004 |
| JP | 2004-97651 | 4/2004 |
| JP | 2005-20097 A | 1/2005 |
| JP | 2005-92281 | 4/2005 |
| JP | 2005-301453 | 10/2005 |
| JP | 2005-309502 A | 11/2005 |
| JP | 2005-333477 A | 12/2005 |

OTHER PUBLICATIONS

Official Letter of Inquiry mailed on Mar. 12, 2013, issued for JP Application No. 2006-275255 (with English translation).
Office Action mailed Jul. 16, 2013 in Japanese Patent Application No. 2012-158825 (with English Translation).
Japanese Office Action mailed on Aug. 9, 2011 issued for JP Application No. 2006-275255, filed on Oct. 6, 2006 (with English translation).

* cited by examiner

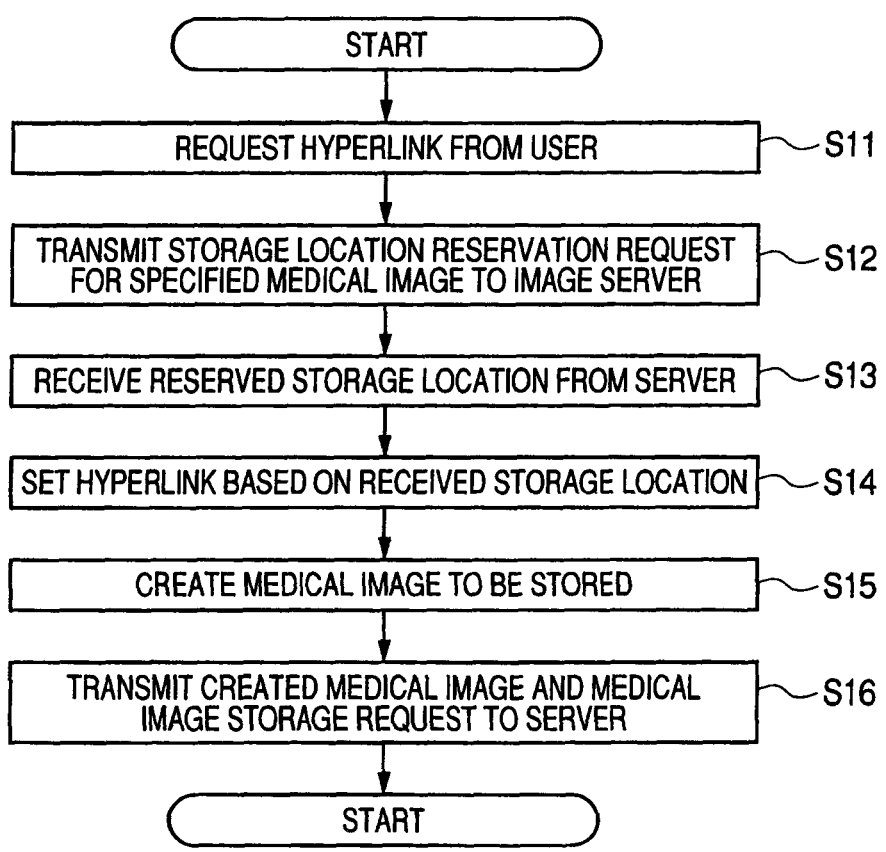

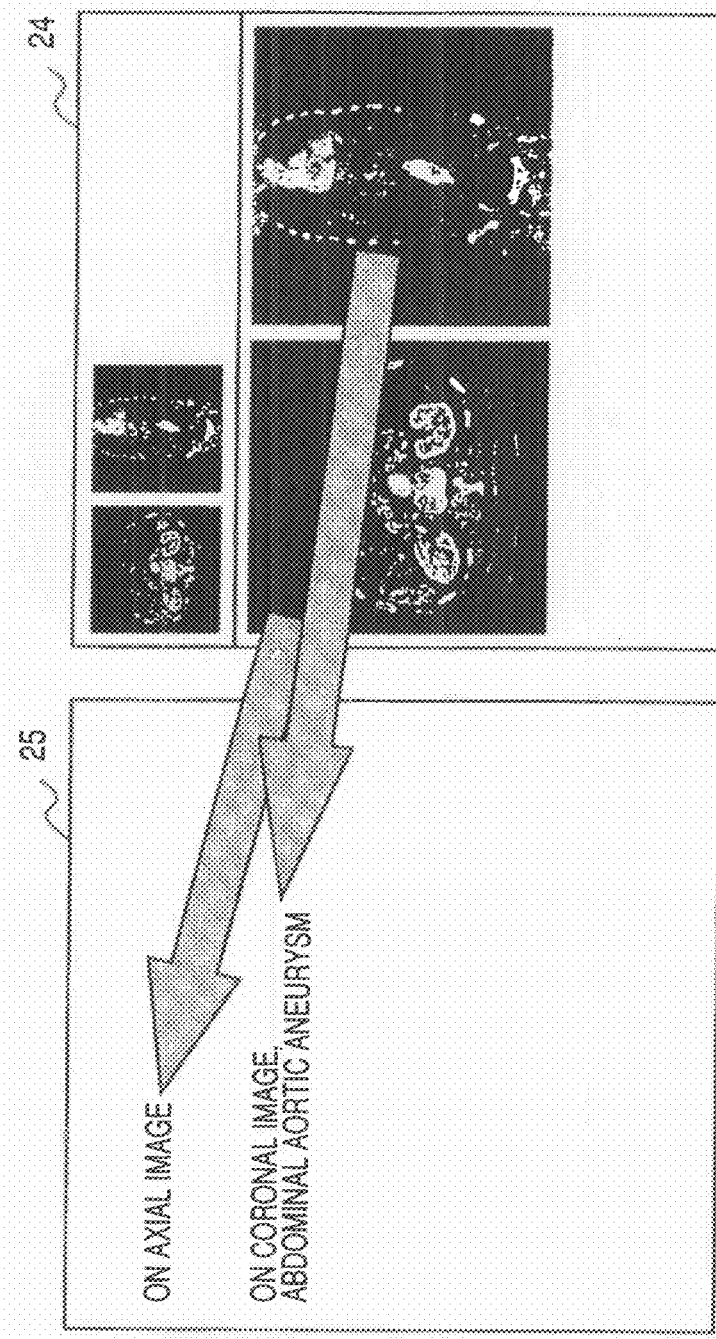

MEDICAL IMAGE INFORMATION SYSTEM, IMAGE SERVER AND CLIENT

CROSS-REFERENCE TO RELATED APPLICATIONS

This application is based upon and claims the benefit of priority from prior Japanese Patent Application No. 2006-275255, filed Oct. 6, 2006, the entire contents of which are incorporated herein by reference.

BACKGROUND OF THE INVENTION

1. Field of the Invention

The present invention relates to a medical image information system, an image server and a client, and more particularly, to a technique for associating a medical image with a diagnosis report.

2. Description of the Related Art

Medical image information systems have been put into practical use, each of which has an image server to store medical images produced by a medical image diagnosis apparatus such as an X-ray CT apparatus, an MRI apparatus or the like, an image viewer to display the stored medical images to be read by a doctor or the like, a report system to make a diagnosis report based on a result of the reading by the doctor or the like. In such medical image information systems, the doctor or the like prepares a diagnosis report by writing his/her opinions on the medical images displayed on the image viewer in an opinion column of the diagnosis, writing a result of diagnosis based on his/her opinions in a diagnosis column, and, if necessary, appending the medical images to the diagnosis report.

In connection with such medical image information systems, for example, JP-A-2005-301453 discloses that hyperlinks for link information on medical images stored in an image server are set for character strings specified in a diagnosis report. By setting the hyperlinks, it is possible to associate the diagnosis report with the medical images and start up an image viewer to display the medical images from the diagnosis.

Information on a storage location (path) of the medical images is necessary to set the hyperlinks in the diagnosis. Therefore, the hyperlinks can be essentially set only for the medical images that have been already stored in the image server. Accordingly, in order to set hyperlinks for medical images newly produced in the image viewer by a doctor or the like, it is necessary to set the hyperlinks in the diagnosis report after storing the produced new medical images in the image server. This may result in lowering of diagnosis efficiency.

BRIEF SUMMARY OF THE INVENTION

An advantage of the invention is that it provides a medical image information system which is capable of setting link information in a diagnosis report without medical images stored in an image server, an image server and a client.

According to a first aspect of the invention, there is provided a medical image information system that prepares a diagnosis report for which link information for referring to a medical image stored in an image server is set, and displays a medical image not stored in the image server, including: a reservation request unit that makes a storage location reservation request for the medical image not stored in the image server prior to storing the medical image not stored in the image server; a reservation unit that receives the storage location reservation request and makes reservation for storage location of the medical image not stored in the image server; and a link information setting unit that sets the link information for the reserved storage location.

According to a second aspect of the invention, there is provided an image server that stores a medical image having link information set for a diagnosis report in a client, including: a reservation unit that receives a medical image storage location reservation request from the client and makes reservation for storage location of the medical image; a memory unit that memorizes identification information to identify the medical image for which the storage location reservation request is made, and information on the reserved storage location in association of the identification information with the reserved storage location information; an identification unit that identifies whether a medical image requested to be stored from the client is the medical image for which the storage location reservation request is made, based on the identification information, if the medical image is requested to be stored from the client; and a storing unit that stores the medical image requested to be stored from the client in the reserved storage location if it is identified that the medical image requested to be stored from the client is the medical image for which the storage location reservation request is made.

According to a third aspect of the invention, there is provided a client including: a reservation request unit that makes a storage location reservation request for the medical image not stored in the image server prior to storing the medical image not stored in the image server; and a link information setting unit that receives the storage location reservation request and sets link information for the reserved storage location in the image server.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a flow chart illustrating an operation of a client when a user creates a new medical image and sets a hyperlink for the created medical image.

FIG. 6 is a view showing an example of screen display at the time of setting a hyperlink.

DETAILED DESCRIPTION OF THE INVENTION

Hereinafter exemplary embodiments of the invention will be described with reference to the accompanying drawings.

Figure 1:
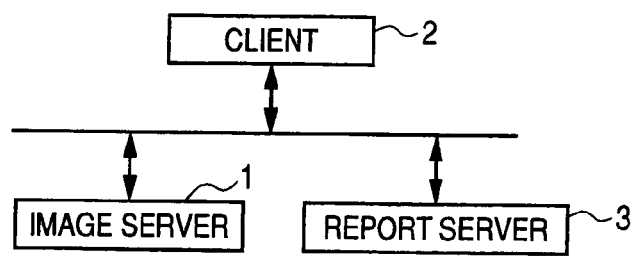
FIG. 1 is a view showing a main configuration of a medical image information system according to an embodiment of the invention.

FIG. 1 is a view showing a main configuration of a medical image information system according to an embodiment of the invention. The medical image information system as shown in FIG. 1 generally includes an image server 1, a client 2 and a report server 3 which are depicted in the form of a block. In FIG. 1, the blocks are shown to be interconnected to allow data communication among them.

Figure 2:
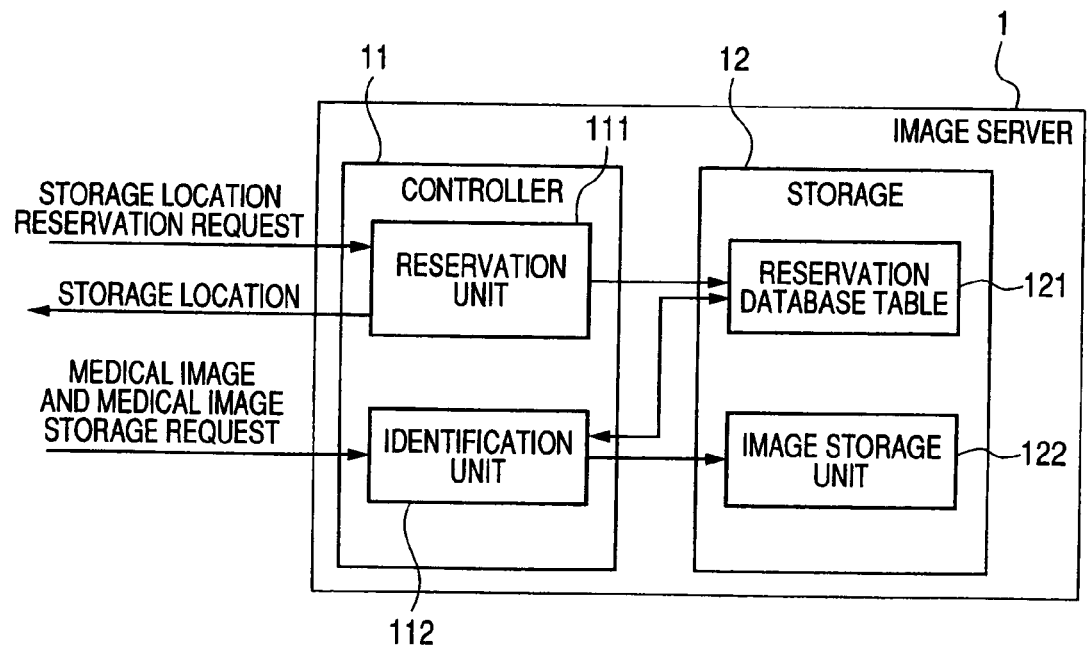
FIG. 2 is a block diagram showing a detailed configuration of an image server.

The image server 1 stores and manages medical images acquired by a medical image diagnosis apparatus (not shown) such as an X-ray CT apparatus, an MRI apparatus, a supersonic diagnosis apparatus or the like. FIG. 2 is a block diagram showing a detailed configuration of the image server 1. As shown in FIG. 2, the image server 1 includes a controller 11 and a storage 12.

The controller 11 controls an operation of the image server 1, such as storing a medical image and information relating to the medical image, which are sent with a medical image storing request from the client 2, in the storage 12. In this embodiment, the controller 11 includes a reservation unit 111 and an identification unit 112. The reservation unit 111 receives a storage location reservation request for a medical image, which is not stored in the storage 12 and is transmitted from the client 2, and makes reservation for a storage location of the medical image in order to set a hyperlink for the medical image. The identification unit 112 identifies whether or not the medical image newly transmitted from the client 2 is a medical image whose storage location is reserved, and causes the medical image to be stored in the storage 12 based on a result of the identification. The reservation unit 111 and the identification unit 112 will be described in more detail later in terms of their function.

The storage 12 includes a database (DB) for storing a reservation database table 121 to associate a storage location prepared according to the storage location reservation request from the client 2 with the medical image to be stored in the prepared storage location, and an image storage unit 122 for storing the medical image and medical image-related information (for example, user identification (UID) to identify the medical image, examination date, information on a patient, etc., which are required to search the medical image in the future).

Figure 3:
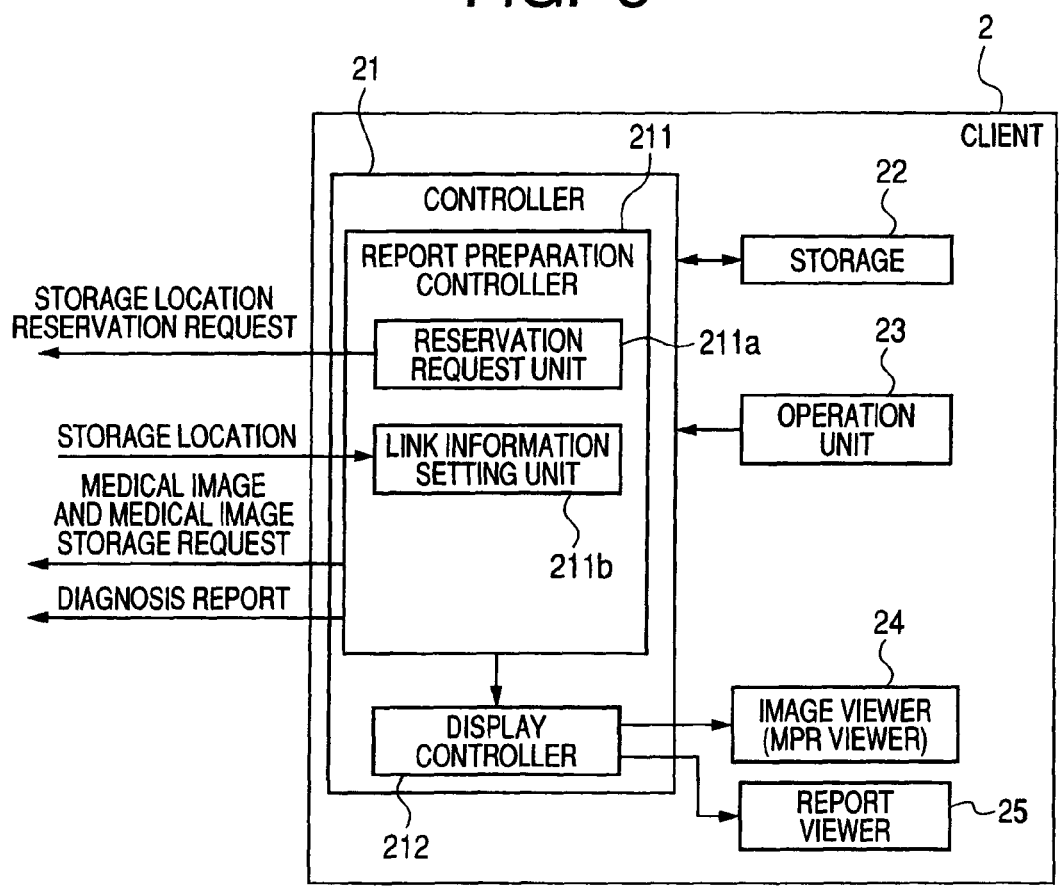
FIG. 3 is a block diagram showing a detailed configuration of a client.

The client 2 is a terminal for preparing an electronic diagnosis report based on an operation input from a user such as a doctor. FIG. 3 is a block diagram showing a detailed configuration of the client 2. As shown in FIG. 3, the client 2 includes a controller 21, a storage 22, an operation unit 23, an image viewer 24 and a report viewer 25.

The controller 21 controls operation of the blocks of the client 2 according to manipulation of the operation unit 23. In this embodiment, the controller 21 includes a report preparation controller 211 and a display controller 212. The report preparation controller 211 controls various processes relating to preparation of a diagnosis report according to a diagnosis report preparation program stored in the storage 22. In this embodiment, the report preparation controller 211 includes a reservation request unit 211a and a link information setting unit 211b. The reservation request unit 211a requests the image server 1 to make reservation for storage location of a medical image, which is not stored in the storage 12 of the image server 1, in order to set a hyperlink for the medical image. The link information setting unit 211b sets a hyperlink for a character string of a diagnosis report, which is set by a doctor or the like. The display controller 212 performs a control in such a manner to display a diagnosis report and a diagnosis report preparation screen on the report viewer 25 according to the diagnosis report preparation program stored in the storage 22 or display the medical image, which is transmitted from the image server 1, and a medical image edition screen on the image viewer 24 according to a medical image display program stored in the storage 22.

The storage 22 stores the diagnosis report preparation program and the medical image display program, and temporarily stores the medical image transmitted from the image server 1. An example of the operation unit 23 may include a keyboard for inputting characters on the diagnosis report preparation screen, a mouse for performing various designation operations, etc.

The image viewer 24 may include, for example, a liquid crystal display monitor or the like for displaying the medical image and the medical image edition screen under control of the display controller 212. The report viewer 25 may include, for example, a liquid crystal display monitor or the like for displaying the diagnosis report and the diagnosis report edition screen under control of the display controller 212. It is possible for the doctor or the like to prepare the diagnosis report on the diagnosis report preparation screen displayed on the report viewer 25 while viewing the medical image displayed on the image viewer 24. In this embodiment, it is possible to set a hyperlink for link information for associating a character string in the diagnosis report with data on the medical image in the image server 1.

The image viewer 24 not only display the medical image transmitted from the image server 1, as it is, but also has a function as an MPR viewer for preparing and displaying an image viewed from a different section of the medical image transmitted from the image server 1 according to manipulation of the operation unit 23 by the doctor or the like.

The report server 3 associates the diagnosis report prepared in the client 2 with information relating to the diagnosis report (UID to specify the diagnosis report, etc.) and store it. Details of the report server 3 will be omitted for the sake of brevity.

Figure 4:
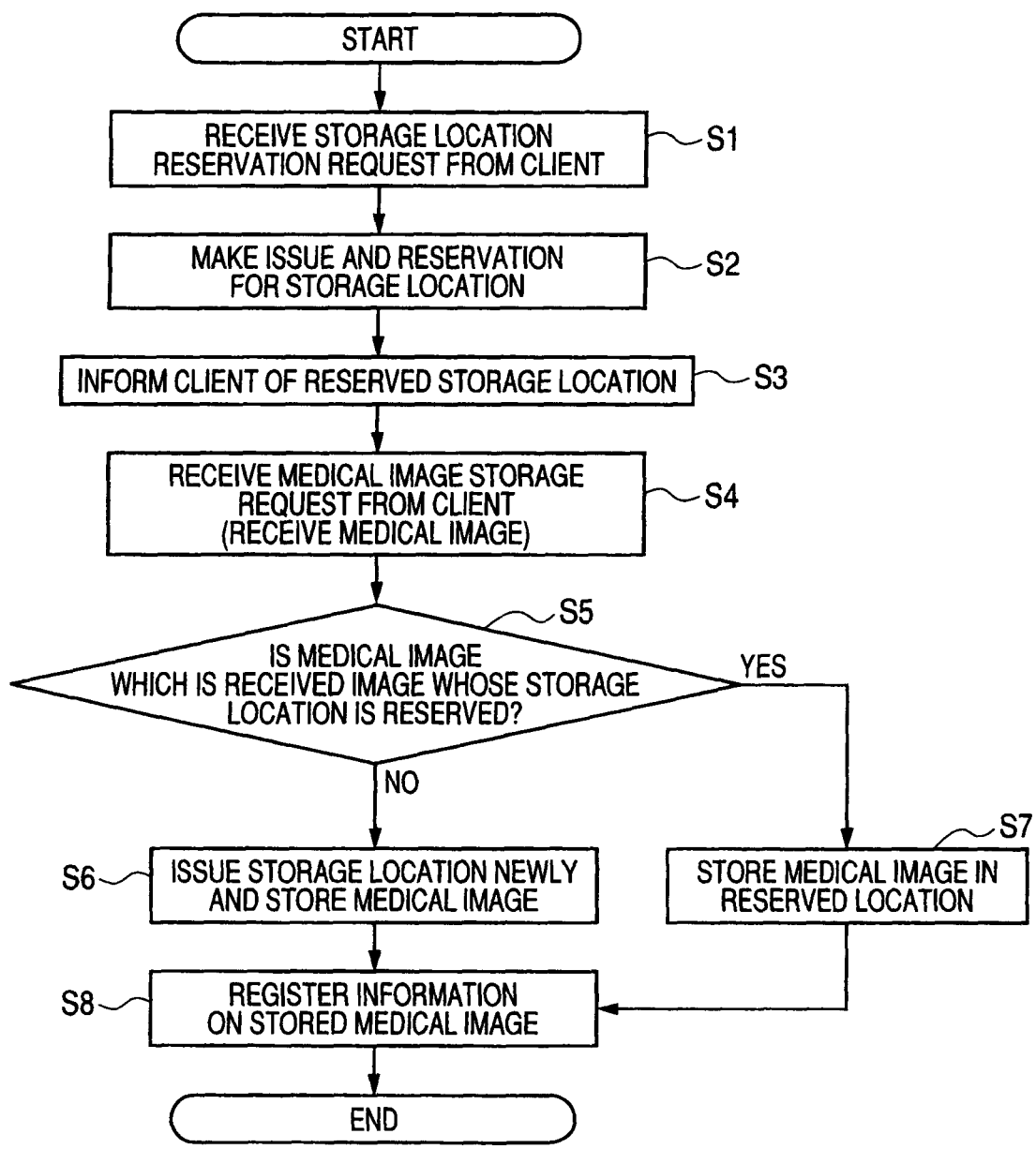
FIG. 4 is a flow chart illustrating an operation of an image server when a user creates a new medical image and sets a hyperlink for the created medical image.

Hereinafter, the operation of this embodiment will be described. FIG. 4 is a flow chart illustrating an operation of the image server 1 when a user creates a new medical image (for example, an MPR image) and sets a hyperlink for the created medical image. FIG. 5 is a flow chart illustrating an operation of the client 2 when a user creates a new medical image and sets a hyperlink for the created medical image.

To begin with, a doctor or the like prepares a diagnosis report while viewing a medical image displayed on the image viewer 24. At this time, when it is instructed to set a hyperlink through manipulation of the operation unit 23 by the doctor or the like (Step S11), the reservation request unit 211a of the client 2 sends a storage location reservation request to reserve a storage location in which a medical image to be hyperlinked is stored to the image server 1 (Step S12). The sent storage location reservation request contains image-specifying information (for example, an image UID, etc.) to specify a medical image to be created later. The instruction to set the hyperlink may be made by dragging and dropping a medical image, which is displayed on the image viewer 24, on a character string in a diagnosis report displayed on the report viewer 25, for example, as shown in FIG. 6.

Upon receiving the storage location reservation request from the client 2 (Step S1), the reservation unit 111 of the image server 1 makes issue and reservation for storage location in the image storage unit 122 (Step S2). The image server 1 registers the image-specifying information contained in the storage location reservation request and information on the storage location in the reservation database table 121 of the storage 12, with the image-specifying information associated with the storage location information. When the reservation of the storage location is completed, the reservation unit 111 of the image server 1 informs the client 2 of the information on the reserved storage location (Step S3).

Upon receiving the storage location information from the image server 1 (Step S13), the link information setting unit 211*b* of the client 2 sets a hyperlink for the received storage location information (Step S14). An example of information set for the hyperlink may include information for specifying an original image used to prepare the medical image, information on display conditions of a corresponding medical image when a character string for which the hyperlink is set is designated in the diagnosis report, etc., in addition to the storage location information of the medical image.

Thereafter, when a user creates a medical image (for example, an MPR image) newly stored in the image server 1 (Step 15), the report preparation controller 211 of the client 2 transmits the created medical image, along with a medical image storage request, to the image server 1 (Step S16), completing a process at a side of the client 2. Here, the image-specifying information issued in Step S12 is contained in the medical image storage request. After the diagnosis report is prepared in the client 2, the prepared diagnosis report is stored in the report server 3.

Upon receiving the medical image and the medical image storage request from the client 2 (Step S4), the identification unit 112 of the image server 1 determines whether or not the received medical image is an image whose storage location is reserved, from the image-specifying information contained in the medical image storage request (Step S5). In the determination at Step S5, if the received image-specifying information is not registered in the reservation database table 121, that is, if the received medical image is not an image whose storage location is reserved, the identification unit 112 of the image server 1 issues a new storage location and stores the received medical image in the issued storage location (Step S6). On the other hand, in the determination at Step S5, if the received image-specifying information is registered in the reservation database table 121, that is, if the received medical image is an image whose storage location is reserved, the identification unit 112 of the image server 1 stores the received medical image in the reserved storage location (Step S7). After the storage of the medical image is completed, the identification unit 112 of the image server 1 stores medical image-related information (for example, an image UID, examination date, information on a patient, etc., which are required to search the medical image in the future) in the image storage unit 122 (Step S8), completing a process at a side of the image server 1.

As described above, according to this embodiment, prior to setting the hyperlink actually, the storage location is reserved according to the storage location reservation request for the image server 1 from the client 2. The hyperlink is set for the reserved storage location. Thereafter, since the medical image transmitted to image server 1 is stored in the reserved storage location, it is possible to set the hyperlink although the medical image was not stored in the image server 1.

Although it has been illustrated in this embodiment that the medical image is created after the hyperlink is set, the hyperlink may be set after the medical image is created. In this case, since the medical image was actually created, for example, information on image size may also be contained in the storage location reservation request and transmitted, in addition to the image UID.

In addition, in this embodiment, although the client 2 issues the image-specifying information such as the image UID, the client 2 may make the storage location reservation request only, and the image-specifying information may be issued in the image server 1.

In addition, in the embodiment, in addition to the medical image whose storage location is reserved, all medical images created and displayed in the image viewer 24 may be stored in the image server 1. In addition, if the medical image whose storage location is reserved is, for example, a CT image, an MPR image created in a batch process based on a slice pitch or number set in a range set from images at front and rear slice positions may be stored in the image server 1.

When the storage location is reserved, the image server 1 may store a dummy image in the reserved storage location. The dummy image refers to an image for informing a user that the storage location is reserved, for example. By storing such a dummy image, although a medical image is actually not stored, since the dummy image is displayed when a hyperlinked character string is designated, a user can confirm whether or not a hyperlink is correctly set before the storage of the medical image is completed.

In addition, when the image server 1 is requested to store a medical image whose storage location is reserved, the image server 1 may store the medical image in preference to other medical images whose storage locations are not reserved. This priority may be determined by the image server 1 or may be designated by the client 2. In this manner, by preferentially storing the medical image whose storage location is reserved, the hyperlink can be smoothly set even if the image server 1 has high load due to registration of a mass of images.

In addition, although the hyperlinked medical image has been illustrated with the MPR image in this embodiment, the subject invention is not limited thereto. For example, the hyperlink setting method of this embodiment may be applied to a differential image of a plurality of medical images, an image obtained by subjecting a gray scale process to an original medical image, etc.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image information system that prepares a diagnosis report in which a hyperlink link to a medical image stored in an image server is set, and displays a medical image not stored in the image server, comprising:
    a processor;
    a reservation request unit that, in conjunction with the processor, makes a storage location reservation request for the medical image not stored in the image server prior to storing the medical image not stored in the image server;
    a reservation unit that, in conjunction with the processor, receives the storage location reservation request and makes reservation for storage location of the medical image not stored in the image server; and
    a link information setting unit that, in conjunction with the processor, sets the hyperlink for the reserved storage location,
    wherein the reservation unit temporarily stores a dummy image for which the storage location reservation request is made, in the storage location of the image server when the reservation for storage location is made.

2. The medical image information system according to claim 1, further comprising:
    a memory unit that stores identification information to identify the medical image for which the storage location reservation request is made, and information on the reserved storage location in association of the identification information with the reserved storage location information;

an identification unit that identifies whether a medical image requested to be stored is the medical image for which the storage location reservation request is made, based on the identification information; and a storing unit that stores the medical image requested to be stored in the reserved storage location if the identification unit identifies that the medical image requested to be stored is the medical image for which the storage location reservation request is made.

3. The medical image information system according to claim 1, wherein the link information setting unit additionally sets display conditions to display the medical image not stored in the image server and information to specify an original medical image used to create the medical image not stored in the image server, in the hyperlink.

4. The medical image information system according to claim 1, wherein the reservation request unit makes a storage location reservation request for a plurality of medical images not stored in the image server.

5. The medical image information system according to claim 2, wherein the storing unit stores the medical image whose storage location is reserved in preference to the medical image whose storage location is not reserved.

6. The medical image information system according to claim 1, further comprising:

a memory unit that stores identification information, before the medical image is stored in the reserved storage location, that identifies the medical image for which the storage location reservation request is made, and information on the reserved storage location in association of the identification information with the reserved storage location information;

an identification unit that identifies whether a medical image requested to be stored in the reserved storage location is the medical image for which the storage location reservation request is made, based on a comparison of the identification information stored in the memory unit and an identifier of the medial image requested to be stored; and a storing unit that stores the medical image requested to be stored in the reserved storage location in response to the identification unit identifying that the medical image requested to be stored is the medical image for which the storage location reservation request is made, and the storing unit stores the medical image requested to be stored in location different from the reserved storage location in response to the identification unit identifying that the medical image requested to be stored is not the medical image for which the storage location reservation request is made.

7. The medical image information system according to claim 1, wherein said dummy image holds an entirety of the reserved storage location.

* * * * *